(12) United States Patent
Ishikawa et al.

(10) Patent No.: US 7,521,581 B2
(45) Date of Patent: Apr. 21, 2009

(54) CATALYST COMPOSITION AND PROCESS FOR PRODUCING CROSS-COUPLED COMPOUND USING SAME

(75) Inventors: Shinichi Ishikawa, Shunan (JP); Hiroshi Awano, Shunan (JP); Hirokazu Yano, Shunan (JP); Hisao Equchi, Shunan (JP)

(73) Assignee: Tosoh Corporation, Shunan-shi (JP)

( * ) Notice: Subject to any disclaimer, the term of this patent is extended or adjusted under 35 U.S.C. 154(b) by 348 days.

(21) Appl. No.: 11/391,567

(22) Filed: Mar. 29, 2006

(65) Prior Publication Data
US 2006/0224011 A1 Oct. 5, 2006

(30) Foreign Application Priority Data
Mar. 30, 2005 (JP) ............................. 2005-099187

(51) Int. Cl.
C07C 49/105 (2006.01)
(52) U.S. Cl. ...................................... 568/369; 560/104
(58) Field of Classification Search ................. 558/369; 560/104
See application file for complete search history.

(56) References Cited

U.S. PATENT DOCUMENTS

| 6,407,289 B1 | 6/2002 | Russo-Rodriguez et al. |
| 2003/0162950 A1 | 8/2003 | Itahashi et al. |
| 2004/0181018 A1 | 9/2004 | Weiss |
| 2005/0113610 A1* | 5/2005 | Sakurai et al. ............. 570/227 |
| 2006/0058178 A1 | 3/2006 | Kempe et al. |

FOREIGN PATENT DOCUMENTS

| EP | 0 978 499 A2 | 2/2000 |
| EP | 1 489 063 A1 | 12/2004 |
| JP | 2000-302697 A | 10/2000 |
| JP | 2000-302720 A | 10/2000 |
| JP | 2003-119175 A | 4/2003 |
| JP | 2004-91467 A | 3/2004 |
| WO | WO-03/043735 A2 | 5/2003 |

OTHER PUBLICATIONS

Leadbeater et al., Suzuki Aryl Couplings Mediated by Phosphine-Free Nickel Complexes, Tetrahedron 55 (1999) 11889-11894.*
Kotha et al., Tetrahedron report No. 625, vol. 58, No. 48, pp. 9633-9695, (Nov. 25, 2002).
Kondo et al., Tetrahedron Letters 44, vol. 44, No. 49, pp. 8801-8804, (Dec. 1, 2003).
Tetrahedron Letters, vol. 37, No. 17, (1996), pp. 2993-2996.
Tetrahedron Letters, vol. 38, No. 20, (1997), pp. 3513-3516.
J. Org. Chem., vol. 62, (1997), pp. 8024-8030.
Tetrahedron, vol. 55, (1999), pp. 11889-11894.

* cited by examiner

*Primary Examiner*—Daniel M Sullivan
*Assistant Examiner*—Chukwuma O Nwaonicha
(74) *Attorney, Agent, or Firm*—Birch, Stewart, Kolasch & Birch, LLP

(57) ABSTRACT

A catalyst composition for a cross-coupling reaction comprising a nickel salt-amine complex of formula (1), and triphenylphosphine.

$$R^1\underset{R^2}{\overset{}{N}}\underset{}{(CH_2)_n}\underset{R^4}{\overset{}{N}}\underset{Ni}{\overset{R^3}{}}\underset{X\ \ X}{} \quad (1)$$

where $R^1$ thru $R^4$ independently represent alkyl, aryl, heteroaryl or alkenyl; n is an integer of 1-6; and X independently represents halo, hydroxyl, nitrate or acetate group. Using the catalyst composition, a cross-coupling reaction is carried out between a boron-containing compound of formula (2) and a compound of formula (3).

$$R^5-B\overset{Y}{\underset{Y}{\diagdown}} \quad (2)$$

$$R^6-Z \quad (3)$$

where $R^5$ and $R^6$ are the same as $R^1$-$R^4$ defined above; Y independently represents hydroxyl or alkoxy, Z is halo, methanesulfonate or trifluoromethanesulfonate.

8 Claims, No Drawings

CATALYST COMPOSITION AND PROCESS FOR PRODUCING CROSS-COUPLED COMPOUND USING SAME

TECHNICAL FIELD

This invention relates to a catalyst composition exhibiting a high catalytic activity for a cross-coupling reaction in organic syntheses, and a process for producing a coupled compound using the catalyst composition.

Various functional compounds can be produced with an enhanced efficiency by the process according to the present invention. For example, 4-hydroxy-4'-cyanobiphenyl widely used for liquid crystal or as a raw material for medicines can be produced with an enhanced efficiency.

BACKGROUND ART

The technique utilizing a coupling reaction is important for the synthesis of electronic materials, intermediates for medicines and pesticides, and various functional compounds. Among others, a technique utilizing a coupling reaction wherein a boron-containing compound is allowed to react with an organic halide compound in the presence of a base and a catalyst attracts widespread attention (which reaction is hereinafter referred to as "Suzuki coupling reaction" when appropriate) as a broadly applicable synthesis technique. In recent years, Suzuki coupling reaction has become very important for the synthesis of biaryl compounds for use as intermediates for medicines and pesticides and as a material for liquid crystal, and synthesis of substituted olefin compounds for use as a raw material for functional materials.

Heretofore, the synthesis of biaryl compounds and substituted olefin compounds according to Suzuki coupling reaction has been widely carried out using a catalyst comprised of a palladium salt and a phosphine compound (hereinafter abbreviated to as "palladium-phosphine catalyst"). However, palladium is expensive and, when less expensive raw materials such as chlorides are used for the cross-coupling reaction using the palladium-phosphine compound, the reaction does not proceed at a desired rate.

As less expensive substitutes for the expensive palladium-phosphine catalyst, catalysts each comprised of a nickel salt and a phosphine compound (hereinafter abbreviated to as "nickel-phosphine catalyst") has been proposed in, for examples, Japanese Unexamined Patent Publication (hereinafter abbreviated to as "JP-A") 2000-302697, JP-A 2000-302720, JP-A 2003-119175 and JP-A 2004-91467; and Tetrahedron Letters, England, 1996, vol. 37, p 2993-2996 (see scheme 1, tables 1 and 2), Journal of Organic Chemistry, USA, 1997, vol. 62, p 8024-8030 (see scheme 1, Tables 1-6), and Tetrahedron Letters, England, 1997, vol. 38, p 3513-3516 (see scheme 1, tables 1 and 2). However, these proposed catalysts have problems such that a phosphine ligand such as 1,2-bis(diethylphosphino)ethane which is expensive and has poor stability and poor handling properties must be used in combination with a nickel compound for carrying out the reaction with good efficiency, and occasionally a reducing agent such as butyllithium which is also expensive and has poor handing properties must be used.

Recently, a catalyst comprised of a nickel compound with an amine compound (hereinafter referred to as "nickel-amine compound") attracts attention (for example, JP-A 2004-91465 and Tetrahedron, England, 1999, vol. 55, p 11889-11894 (see FIG. 1-FIG. 3, tables 1-3). This catalyst has a problem such that an expensive amine compound such as 1,8-diazabicyclo[5.4.0]-7-undecene must be used in combination with said catalyst to enhance the yield to a desired level, and that bis(1,5-cyclooctadiene)nickel as used as the nickel compound is very sensitive to air and difficult to handle in the air, and thus, is not suitable for commercial use.

Further, nickel catalysts commonly have a problem such that a strong base such as potassium phosphate must be used in combination with the nickel catalyst which is expensive and tends to cause decomposition reaction of a boronic acid raw material.

DISCLOSURE OF THE INVENTION

An object of the present invention is to provide a catalyst composition having high activity for a cross-coupling reaction utilized in organic syntheses.

Another object of the present invention is to provide a process for producing a cross-coupled compound with an enhanced efficiency by utilizing said catalyst composition.

The present inventors made extensive research to solve the foregoing problems of the prior art, and have found that a catalyst composition comprising a specific complex of a nickel salt with an amine compound, and triphenylphosphine exhibits very high activity for cross-coupling reaction, especially for Suzuki coupling reaction.

In accordance with the present invention, there is provided a catalyst composition for a cross-coupling reaction comprising a complex of a nickel salt with an amine compound, represented by the following formula (1), and triphenylphosphine.

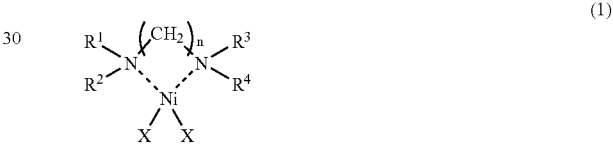

(1)

wherein $R^1$ through $R^4$ may be the same or different and represent a substituted or unsubstituted linear, branched or cyclic alkyl group, a substituted or unsubstituted aryl group, a substituted or unsubstituted heteroaryl group, or a substituted or unsubstituted linear, branched or cyclic alkenyl group; n is an integer of 1 to 6; and X may be the same or different and each X represents a halogen atom, a hydroxyl group, a nitrate group or an acetate group.

Further there is provided a process for producing a cross-coupled compound represented by the following formula (4):

(4)

wherein $R^5$ and $R^6$ may be the same or different and represent a substituted or unsubstituted linear, branched or cyclic alkyl group, a substituted or unsubstituted aryl group, a substituted or unsubstituted heteroaryl group, or a substituted or unsubstituted linear, branched or cyclic alkenyl group;

which comprises allowing a boron-containing compound represented by the following formula (2) to react with a compound represented by the following formula (3):

wherein $R^5$ and $R^6$ are as defined above: Y may be the same or different and each Y represents a hydroxyl group or an alkoxy group, provided that, when each Y is a hydroxyl group, three boron-containing compounds may be dehydration-condensed to form a trimer anhydride, and that, when two Y are an alkoxy group, the two Y may be bonded together to form a ring; and Z represents a halogen atom, a methanesulfonate group or a trifluoromethane-sulfonate group;

in the presence of a base and the above-mentioned catalyst composition.

DETAILED DESCRIPTION OF THE INVENTION

The present invention will now be described in detail.

Catalyst Composition

The catalyst composition according to the present invention comprises a complex of a nickel salt with an amine compound, and triphenylphosphine.

The nickel salt refers to a nickel salt of an acid, wherein the valence of nickel is, for example, in the range of 0 to 2. The nickel salt is not particularly limited, and, as specific examples thereof, there can be mentioned nickel halides such as nickel(II) fluoride, nickel(II) chloride, nickel(II) bromide and nickel(II) iodide; nickel(0) powder; nickel salts of inorganic acid such as nickel(II) sulfate, nickel(II) nitrate, nickel(II) perchlorate and nickel(II) sulfide; and nickel salts of organic acid such as nickel(II) formats, nickel(II) oxalate, nickel(II) acetate, nickel(II) fumarate, nickel(II) lactate, nickel(II) gluconate, nickel(II) benzoate, nickel(II) stearate, nickel(II) sulfamate, nickel(II) amidosulfate, nickel(II) carbonate and nickel(II) acetylacetonato.

The nickel salts may be used either alone or as a combination of at least two thereof. Of the above-recited nickel salts, nickel halides are preferable for cost consideration and from a viewpoint of their availability, reactivity and stability The amine compound as used in the catalyst composition of the present invention refers to a tertiary bidentate amine compound represented by the following formula (9):

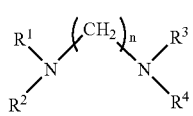

(9)

wherein $R^1$ through $R^4$ may be the same or different and represent a substituted or unsubstituted linear, branched or cyclic alkyl group, a substituted or unsubstituted aryl group, a substituted or unsubstituted heteroaryl group, or a substituted or unsubstituted linear, branched or cyclic alkenyl group. n is an integer of 1 to 6.

As specific examples of the tertiary bidentate amine compound of formula (9), there can be mentioned N,N,N',N'-tetramethylmethanediamine, N,N,N',N'-tetraethylmethanediamine, N,N,N',N'-tetramethylethylenediamine, N,N,N',N'-tetramethylpropylenediamine, N,N,N',N'-tetramethylhexanediamine, N,N,N',N'-tetraethylethylenediamine, N,N,N',N'-tetraethylpropylenediamine, N,N,N',N'-tetraethylhexanediamine, N,N,N',N'-tetraphenylethylenediamine, N,N,N',N'-tetraphenylpropylenediamine, N,N,N',N'-tetraphenylhexanediamine, N,N-dimethyl-N',N'-diethylethylenediamine, N,N-dimethyl-N',N'-diethylpropanediamine and N,N-dimethyl-N', N'-diethylhexanediamine. Of these, N,N,N',N'-tetramethylethylenediamine is preferable from a cost consideration and in view of yield and availability.

In the catalyst composition according to the present invention, triphenylphosphine is used in combination with the complex of a nickel salt with an amine compound. If other phosphines are used instead, a catalyst composition having the desired high activity for cross-coupling reaction cannot be obtained.

The catalyst composition according to the present invention can be prepared by incorporating triphenylphosphine with the complex of a nickel salt with an amine compound. Alternatively a nickel salt, an amine compound and triphenylphosphine can be incorporated in a reaction mixture wherein a nickel-amine complex is formed in the reaction mixture and thus, the catalyst composition of the present invention is obtained. The ratio in amounts of the three ingredients is such that the amount of amine compound is appropriately chosen in the range of 1.0 to 10.0 moles, more preferably 1.0 to 5.0 moles, and the amount of triphenylphosphine is appropriately chosen in the range of 1.0 to 10.0 moles, more preferably 2.0 to 5.0 moles, per mole of the nickel salt.

The catalyst composition can be prepared in the presence of a solvent. The solvent used is not particularly limited, provided that it is inactive for the nickel salt, the amine compound and triphenylphosphine. The solvent includes, for example, ether solvents, oxygen-containing solvents, nitrogen-containing solvents, aromatic hydrocarbon solvents and aliphatic hydrocarbon solvents. These solvents may be used either alone or as a combination of at least two thereof.

Cross-Coupling Reaction

The process according to the present invention involves a Suzuki coupling reaction wherein a cross-coupled compound represented by the following formula (4):

$$R^5\!\!-\!\!R^6 \qquad (4)$$

is produced by allowing a boron-containing compound represented by the following formula (2) to react with a compound represented by the following formula (3):

(2)

(3)

in the presence of a base and the above-mentioned catalyst composition.

In the formulae (4), (2) and (3), $R^5$ and $R^6$ may be the same or different and represent a substituted or unsubstituted linear, branched or cyclic alkyl group, a substituted or unsubstituted aryl group, a substituted or unsubstituted heteroaryl group, or a substituted or unsubstituted linear, branched or cyclic alkenyl group. Y may be the same or different and each Y represents a hydroxyl group or an alkoxy group. However, when each Y is a hydroxyl group, three boron-containing compounds may be dehydration-condensed to form a trimer anhydride, and, when two Y are an alkoxy group, the two Y may be bonded together to form a ring. Z represents a halogen atom, a methanesulfonate group or a trifluoromethanesulfonate group.

The boron-containing compound as used in the process according to the present invention is a compound of formula (2) wherein $R^5$ represents a substituted or unsubstituted linear, branched or cyclic alkyl group, a substituted or unsubstituted aryl group, a substituted or unsubstituted heteroaryl group, or a substituted or unsubstituted linear, branched or cyclic alkenyl group.

The substituted or unsubstituted linear, branched or cyclic alkyl group for $R^5$ is not particularly limited and includes, for example, linear, branched or cyclic $C_1$-$C_{20}$ alkyl groups. As specific examples of the linear, branched or cyclic $C_1$-$C_{20}$ alkyl groups, there can be mentioned a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradeayl group, a pentadecyl group, a hexadecyl group, a heptadecyl group, an octadecyl group, a nonadecyl group, an eicosyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, a cyclododecyl group, a oyclotridecyl group, a cyclotetradecyl group, a cyclopentadecyl group, a cyclohexadecyl group, a cycloheptadecyl group, a cyclooctadecyl group, a cyclononadecyl group and a cycloeicosyl group. Further polycyalic alkyl groups such as norbornal group and adamantyl group are also mentioned.

These alkyl groups may have one or more substituents, which include, for example, a halogen atom, a substituted or unsubstituted linear, branched or cyclic alkyl group, a substituted or unsubstituted aryl group, a substituted or unsubstituted heteroaryl group, or a substituted or unsubstituted linear, branched or cyclic alkenyl group, a hydroxyl group, an alkoxy group, an amino group, a cyano group, a carbonyl group, a carboxyl group or an ester group.

The substituted or unsubstituted aryl group for $R^5$ is not particularly limited and includes, for example, substituted or unsubstituted aryl groups having 1 to 4 rings each with 6 to 18 carbon atoms. As specific examples of the substituted or unsubstituted aryl group, there can be mentioned a phenyl group, a naphthyl group, an anthracenyl group, an azulenyl group, a pyrenyl group, a phenanthrenyl group and a fluorenyl group. These aryl groups may have one or more substituents, which include, for example, a halogen atom, a substituted or unsubstituted linear, branched or cyclic alkyl group, a substituted or unsubstituted aryl group, a substituted or unsubstituted heteroaryl group, or a substituted or unsubstituted linear, branched or cyclic alkenyl group, a hydroxyl group, an alkoxy group, an amino group, a oyano group, a carbonyl group, a carboxyl group or an ester group.

The substituted or unsubstituted heteroaryl group for $R^5$ is not particularly limited and includes, for example, substituted or unsubstituted heteroaryl groups having 1 to 4 rings each with 3 to 18 carbon atoms. As specific examples of the substituted or unsubstituted heteroaryl group, there can be mentioned a pyridyl group, a pyrimidyl group, a pyridazinyl group, a pyrazinyl group, a triazinyl group, a benzofuranyl group, an indolyl group, a benzothiophenyl group, a quinolinyl group, an isoquinolinyl group, a carbazolyl group, an acridinyl group, a phenanthrolinyl group and a phenothiazinyl group. These heteroaryl groups may have one or more substituents, which include, for example, a halogen atom, a substituted or unsubstituted linear, branched or cyclic alkyl group, a substituted or unsubstituted aryl group, a substituted or unsubstituted heteroaryl group, or a substituted or unsubstituted linear, branched or cyclic alkenyl group, a hydroxyl group, an alkoxy group, an amino group, a cyano group, a carbonyl group, a carboxyl group or an ester group.

The substituted or unsubstituted linear, branched or cyclic alkenyl group for $R^5$ is not particularly limited and includes, for example, linear, branched or cyclic $C_2$-$C_{20}$ alkenyl groups. As specific examples of the linear, branched or cyclic $C_2$-$C_{20}$ alkenyl groups, there can be mentioned a vinyl group, a propenyl group, a butenyl group, a pentenyl group, a hexenyl group, a heptenyl group, an octenyl group, a nonenyl group, a decenyl group, an undecenyl group, a dodecenyl group, a tridecenyl group, a tetradecenyl group, a pentadecenyl group, a hexadecenyl group, a heptadecenyl group, an octadecenyl group, a nonadecenyl group, an eicosenyl group, a cyclopropenyl group, a cyclobutenyl group, a cyolopentenyl group, a cyclohexenyl group, a oycloheptenyl group, a cyclooctenyl group, a cyclononenyl group, a cyclodecenyl group, a cycloundecenyl group, a cyclododecenyl group, a cyclotridecenyl group, a cyclotetradecenyl group, a cyclopentadecenyl group, a cyclohexadecenyl group, a cycloheptadecenyl group, a oyclooctadecenyl group, a cyclononadecenyl group and a oycloeicosenyl group. Further polycyclic alkenyl groups such as norbornyl group are also mentioned.

These alkenyl groups may have one or more substituents, which include, for example, a halogen atom, a substituted or unsubstituted linear, branched or cyclic alkyl group, a substituted or unsubstituted aryl group, a substituted or unsubstituted heteroaryl group, or a substituted or unsubstituted linear, branched or cyclic alkenyl group, a hydroxyl group, an alkoxy group, an amino group, a cyano group, a carbonyl group, a carboxyl group or an ester group.

Y may be the same or different and each represents a hydroxyl group or an alkoxy group. When each Y is a hydroxyl group, three boron-containing compounds may be dehydration-condensed to form a trimer anhydride as represented by the following formula (10).

(10)

When two Y are an alkoxy group, the two Y may be bonded together to form a ring.

Preferable boron-containing compounds are an aromatic boron-containing compound represented by the following formula (5), and an alkenyl boron-containing compound represented by the following formula (6):

(5)

(6)

wherein $R^7$ through $R^{10}$ may be the same or different and represent a hydrogen atom, a halogen atom, a substituted or unsubstituted linear, branched or cyclic alkyl group, a substituted or unsubstituted aryl group, a substituted or unsubstituted heteroaryl group, or a substituted or unsubstituted linear, branched or cyclic alkenyl group, a hydroxyl group, an alkoxy group, an amino group, a cyano group, a carbonyl group, a carboxyl group or an ester group; provided that two $R^7$s bonded to two adjacent carbon atoms on the benzene ring in the formula (5) may be bonded together to form a condensed ring with the benzene ring, and two adjacent $R^8$ and $R^{10}$ on the alkenyl group in the formula (6) may be bonded together to form a ring, and $R_9$ and $R^{10}$ bonded to the same carbon atom on the alkenyl group in the formula (6) may be bonded together to form a ring, a is an integer of 1 to 5. Y may be the same or different and each Y represents a hydroxyl group or an alkoxy group.

As specific examples of the aromatic boron-containing compound of formula (5), there can be mentioned phenylboronic acid, 2-methylphenylboronic acid, 3-methylphenylboronic acid, 4-methylphenylboronic acid, 2,3-dimethylphenylboronic acid, 2,4-dimethylphenylboronic acid, 2,5-dimethylphenylboronic acid, 2-ethylphenylboronic acid, 4-ethylphenylboronic acid, 4-n-propylphenylboronic acid, 4-isopropylphenylboronic acid, 4-n-butylphenylboronic acid, 4-t-butylphenylboronic acid, 1-naphthylboronic acid, 2-naphthylboronic acid, 2-biphenylboronic acid, 3-biphenylboronic acid, 4-biphenylboronic acid, 2-fluoro-4-biphenylboronic acid, 2-fluorenylboronic acid, 9-fluorenylboronic acid, 9-phenanthrenylboronic acid, 9-anthracenylboronic acid, 1-pyrenylboric acid, 2-trifluoromethylphenylboronic acid, 3-trifluoromethylphenylboronic acid, 4-trifluoromethyl-phenylboronic acid, 3,5-bis(trifluoromethyl)phenylboronic acid, 2-methoxyphenylboronic acid, 3-mathoxyphenylboronic acid, 4-methoxyphenylboronic acid, 2,5-dimethoxyphenylboronic acid, 4,5-dimethoxyphenylboronic acid, 2,4-dimethoxyphenylboronic acid, 2-ethoxyphenylboronic acid, 3-ethoxyphenylboronic acid, 4-ethoxyphenylboronic acid, 2-n-butoxyphenylboronic acid, 3-n-butoxyphenylboronic acid, 4-n-butoxyphenylboronic acid, 2-t-butoxyphenylboronic acid, 3-t-butoxyphenylboronic acid, 4-t-butoxyphenylboronic acid, 4-phenoxyphenylboronic acid, 3,4-methylenedioxyphenylboronic acid, 2-fluorophenylboronic acid, 3-fluorophenylboronic acid, 4-fluorophenylboronic acid, 2,4-difluorophenylboronic acid, 2,5-difluorophenylboronic acid, 4,5-difluorophenylboronic acid, 3,5-difluorophenylboronic acid, 2-chlorophenylboronic acid, 3-chlorophenylboronic acid, 4-chlorophenylboronic acid, 2-bromophenylboronic acid, 3-bromophenylboronic acid, 4-bromophenylboronic acid, 2-formylphenylboronic acid, 3-formylphenylboronic acid, 4-formylphenylboronic acid, 3-formyl-4-methoxyphenylboronic acid, 2-(1-ethoxyethoxy)phenylboronic acid, 3-(1-ethoxyethoxy)phenylboronic acid, 4-(1-ethoxyethoxy)-phenylboronic acid, 2-acetoxyphenylboronic acid, 3-acetoxyphenylboronic acid, 2-cyanophenylboronic acid, 3-cyanophenylboronic acid, 4-cyanophenylboronic acid, 3-nitrophenylboronic acid, 3-acetylphenylboronic acid, 4-acetylphenylboronic acid, 3-trifluoroacetylphenylboronic acid, 4-trifluoroacetylphenylboronic acid, 4-methylthiophenylboronic acid, 4-vinylphenylboronic acid, 3-carboxylphenylboronic acid, 4-carboxylphenylboronic acid, 3-aminophenylboronic acid, 2-(N,N-dimethylamino)phenylboronic acid, 3-(N,N-dimethylamino)phenylboronic acid, 4-(N,N-dimethylamino)phenylboronic acid, 2-(N,N-diethylamino)phenylboronic acid, 3-(N,N-diethylamino)phenylboronic acid, 4-(N,N-diethylamino)phenylboronic acid, 2-(N,N-dimethylaminomethyl)-phenylboronic acid, 4-benzenebis(boronic acid), phenylboronic acid pinacol ester and 4-cyanophenylboronic acid pinacol ester.

As specific examples of the alkenyl boron-containing compound of formula (6), there can be mentioned vinylboronic acid, vinylboronic acid-triethylamine adduct, trans-2-bromomethylvinylboronic acid, trans-2-chloromethylvinylboronic acid, cis-propenylboronic acid, trans-propenylboronic acid, 1-pentenylboronic acid, (E)-5-chloro-1-penteneboronic acid, trans-1-hexen-1-ylboronic acid, trans-2-t-butylvinylboronic acid, trans-2-phenylvinylboronic acid, α-phenylvinylboronic acid, trans-2-(4-chlorophenyl)vinylboronic acid, trans-2-(4-fluorophenyl)vinylboronic acid, trans-1-octen-1-ylboronic acid, trans-2-[4-(trifluoromethyl)phenyl]vinyl-boronic acid, trans-2-(4-methylphenyl)vinylboronic acid, trans-1-nonenylboronic acid, 2-allyl-4,4,5,5-tetramethyl-1,3,2-dioxaborane, vinylboronic acid dibutyl ester, 2-(cis-1-ethyl-1-butenyl)-benzo(1,3,2)dioxaborol, trans-2-(4,4,5,5-tetramethyl-1,3,2-dioxabororan-2-yl)styrene and methyl-3-(4,4,5,5-tetramethyl-1,3,2-dioxabororan-2-yl)-2-octenoate.

As specific examples of $R^6$ in the formula (3), there can be mentioned those which are recited as examples of $R^5$ in the boron-containing compound (2).

Z represents a halogen atom, a methanesulfonate group or a trifluoromethanesulfonate group. The halogen atom includes, for example, a fluorine atom, a chlorine atom, a bromine atom or an iodine atom.

The compound of formula (3) preferably includes an aromatic compound represented by the following formula (7) and an alkenyl compound represented by the following formula (8):

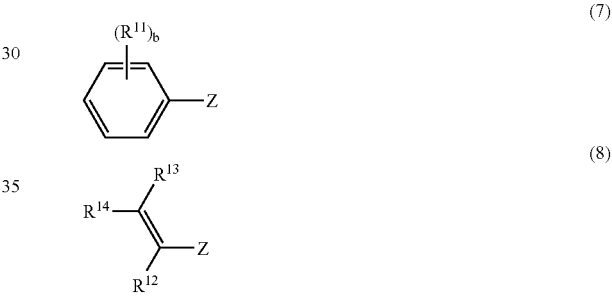

wherein $R^{11}$ through $R^{14}$ may be the same or different and represent a hydrogen atom, a halogen atom, a substituted or unsubstituted linear, branched or cyclic alkyl group, a substituted or unsubstituted aryl group, a substituted or unsubstituted heteroaryl group, or a substituted or unsubstituted linear, branched or cyclic alkenyl group, a hydroxyl group, an alkoxy group, an amino group, a cyano group, a carbonyl group, a carboxyl group or an ester group; provided that two $R^{11}$s bonded to two adjacent carbon atoms on the benzene ring in the formula (7) may be bonded together to form a condensed ring with the benzene ring, and two adjacent $R^{12}$ and $R^{14}$ on the alkenyl group in the formula (8) may be bonded together to form a ring, and $R^{13}$ and $R^{14}$ bonded to the same carbon atom on the alkenyl group in the formula (8) may be bonded together to form a ring. b is an integer of 1 to 5. Z represents a halogen atom, a methanesulfonate group or a trifluoromethanesulfonate group.

As specific examples of the aromatic compound of formula (7), there can be mentioned fluorobenzene, chlorobenzene, bromobenzene, iodobenzene, phenylmethanesulfonate, phenyltrifluoromethanesulfonate, o-chlorotoluene, m-chlorotoluene, p-chlorotoluene, o-bromotoluene, m-bromotoluene, p-bromotoluene, o-iodotoluene, m-iodotoluene, p-iodotoluene, 2-ethylchlorobenzene, 3-ethylchlorobenzene, 4-ethylchlorobenzene, 2-ethylbromobenzene, 3-ethylbromobenzene, 4-ethylbromobenzene, 2-ethyliodobenzene, 3-ethyliodobenzene, 4-ethyliodobenzene, 2-propylchlorobenzene, 3-propylchlorobenzene, 4-propylchlorobenzene, 2-propylbromobenzene, 3-propylbromobenzene, 4-propylbromobenzene, 2-propyliodobenzene, 3-propyliodobenzene, 4-propyliodobenzene, 2-butylchlorobenzene, 3-butylchlorobenzene, 4-butylchlorobenzene, 2-butylbromobenzene, 3-butylbromobenzene, 4-butylbromobenzene, 2-butyliodobenzene, 3-butyliodobenzene, 4-butyliodobenzene, 1-chloronaphthalene, 2-chloronaphthalene, 1-bromonaphthalene, 2-bromonaphthalene, 1-iodonaphthalene, 2-iodonaphthalene, o-dichlorobenzene, m-dichlorobenzene, p-diohlorobenzene, o-dibromobenzene, m-dibromobenzene, p-dibromobenzene, o-bromochlorobenzene, m-bromochlorobenzene, p-bromochlorobenzene, o-chlorofluorobenzene, m-chlorofluorobenzene, p-chlorofluorobenzene, o-bromofluorobenzene, m-bromofluoro benzene, p-bromofluorobenzene, o-chloroanisole, m-chloroanisole, p-chloroanisole, o-bromoanisole, m-bromoanisole, p-bromoanisole, o-iodoanisole, m-iodoanisole, p-iodoanisole, o-chlorophentole, m-chlorophentole, p-ohlorophentole, o-bromophentole, m-bromophentole, p-bromophentole, o-iodophentole, m-iodophentole, p-iodophentole, o-n-butoxychlorobenzene, m-n-butoxychlorobenzene, p-n-butoxychlorobenzene, o-n-butoxybromobenzene, m-n-butoxybromobenzene, p-n-butoxybromobenzene, o-n-butoxyiodobenzene, m-n-butoxyiodobenzene, p-n-butoxyIodobenzene, o-t-butoxychlorobenzene, m-t-butoxychlorobenzene, p-t-butoxychlorobenzene, o-t-butoxyphenylbromide, m-t-butoxyphenylbromide, p-t-butoxyphenylbromide, o-t-butoxyiodobenzene, m-t-butoxyiodobenzene, p-t-butoxylodobenzene, 2-chlorobenzonitrile, 3-chlorobenzonitrile, 4-chlorobenzonitrile, 2-bromobenzonitrile, 3-bromobenzonitrile, 4-bromobenzonitrile, 2-Iodobenzonitrile, 3-iodobenzonitrile, 4-iodobenzonitrile, o-(1-ethoxyethoxy)-chlorobenzene, m-(1-ethoxyethoxy)chlorobenzene, p-(1-ethoxyethoxy)chlorobenzene, o-(1-ethoxyethoxy)bromobenzene, m-(1-ethoxyethoxy)bromobenzene, p-(1-ethoxyethoxy)bromobenzene, o-(1-ethoxyethoxy)iodobenzene, m-(1-ethoxyethoxy)iodobenzene, p-(1-ethoxyethoxy)iodobenzene, o-acetylchlorobenzene, m-acetylchlorobenzene, p-acetylchlorobenzene, o-acetylbromobenzene, m-acetylbromobenzene, p-acetylbromobenzene, o-acetyliodobenzene, m-acetyliodobenzene, p-acetyliodobenzene, o-acetoxychlorobenzene, m-acetoxychlorobenzene, p-acetoxychlorobenzene, o-acetoxybromobenzene, m-acetoxybromobenzene, p-acetoxybromobenzene, o-acetoxyiodobenzene, m-acetoxyiodobenzene, p-acetoxyiodobenzene, 2-trifluoromethylchlorobenzene, 3-trifluoromethylchlorobenzene, 4-trifluoromethylchlorobenzene, 2-trifluoromethylbromobenzene, 3-trifluoromethylbromobenzene, 4-trifluoromethylbromobenzene, 2-trifluoromethyliodobenzene, 3-trifluoromethyliodobenzene, 4-trifluoromethyliodobenzene, 2-chlorobenzoia acid, 3-chlorobenzoic acid, 4-chlorobenzoic acid, 2-bromobenzoic acid, 3-bromobenzoic acid, 4-bromobenzoic acid, 2-iodobenzoic acid, 3-iodobenzoic acid, 4-iodobenzoic acid, methyl 2-chlorobenzoate, methyl 3-chlorobenzoate, methyl 4-chlorobenzoate, methyl 2-bromobenzoate, methyl 3-bromobenzoate, methyl 4-bromobenzoate, methyl 2-iodobenzoate, methyl 3-iodobenzoate, methyl 4-iodobenzoate, 2-chloroaniline, 3-chloroaniline, 4-chloroaniline, 2-bromoaniline, 3-bromoaniline, 4-bromoaniline, 2-iodoaniline, 3-iodoaniline, 4-iodoaniline, 2-chloroformylbenzene, 3-chloroformylbenzene, 4-chloroformylbenzene, 2-bromoformylbenzene, 3-bromoformylbenzene and 4-bromoformylbenzene.

As specific examples of the alkenyl compound of formula (8), there can be mentioned vinyl chloride, vinyl bromide, β-bromostyrene, β-chlorostyrene, β-iodostyrene, α-bromostyrene, α-chlorostyrene, α-iodostyrene, 1-bromo-1-butene, 1-chloro-1-butene, 1-iodo-1-butene, 1-bromo-1-pentene, 1-chloro-1-pentene, 1-iodo-1-pentene, 1-bromo-1-hexene, 1-chloro-1-hexene, 1-iodo-1-hexene, 1-bromo-1-heptene, 1-chloro-1-heptene, 1-iodo-1-heptene, 1-bromo-1-octene, 1-chloro-1-octene, 1-bromo-1-decene, 1-chloro-1-decene and 1-iodo-1-octene.

In the process according to the present invention, a cross-coupling reaction between the boron-containing compound of formula (2) and the compound of formula (3) is carried in the presence of a base.

The base as herein used is not particularly limited, and usually includes inorganic base compounds. As specific examples of the inorganic base compound, there can be mentioned hydroxides such as lithium hydroxide, sodium hydroxide, potassium hydroxide, magnesium hydroxide and calcium hydroxide; carbonic acid salts such as lithium carbonate, sodium carbonate, sodium hydrogencarbonate, potassium carbonate, potassium hydrogencarbonate, magnesium carbonate, calcium carbonate, barium carbonate and cesium carbonate; and phosphoric acid salts such as lithium phosphate, sodium phosphate and potassium phosphate. Organic base compounds can also be used, and, as specific examples thereof, there can be mentioned acetic acid salts such as lithium acetate, sodium acetate, magnesium acetate and calcium acetate; and alkoxides such as lithium methoxide, lithium t-butoxide, sodium methoxide and sodium t-butoxide. Of these, carbonic acid salts are preferable from economic considerations and yield of the cross-coupled product.

The amount of the base is usually in the range of 0.1 to 20 equivalents, based on the above-mentioned boron-containing compound. When the amount of base is smaller than 0.1 equivalent, the cross-coupling does not proceed at a desired rate of reaction. In contrast, when the amount of base is larger than 20 equivalents, the increase in yield of the cross-coupled product becomes minor, and therefore is not advantageous from economic considerations.

The amount of the catalyst composition in the process according to the present invention is in the range of 0.001 to 0.15 equivalent, preferably 0.005 to 0.10 equivalent, as nickel atom, based on the compound of formula (3). When the amount of catalyst composition is smaller than 0.001 equivalent, the cross-coupling does not proceed at a desired rate of reaction. In contrast, when the amount of catalyst composition is larger than 0.15 equivalent, the increase in yield of the cross-coupled product becomes minor, and therefore is not advantageous from economic considerations.

The cross-coupling reaction according to the present invention can be carried out usually at a temperature in the range of 0 to 150° C.

The cross-coupling reaction can be carried out in the presence of a solvent. The solvent used is not particularly limited, and includes, for example, ether solvents, oxygen-containing solvents, nitrogen-containing solvents, aromatic hydrocarbon solvents and aliphatic hydrocarbon solvents. These solvents may be used either alone or as a mixture thereof. A co-solvent such as water can be used.

After completion of the reaction, inorganic compounds produced by side reactions, and unreacted raw materials are removed from the reaction product by means of acid washing, water washing and/or aqueous alkali washing. Further, the reaction product is purified by means of conventional purifying procedures such as chromatography, distillation and/or recrystallization, to give an aimed cross-coupled compound.

EXAMPLES

The invention will now be described specifically by the following examples that by no means limit the scope of the invention.

Example 1

A 50 ml flask flashed with nitrogen gas was charged with 9.7 mg (0.08 mmol) of anhydrous nickel chloride ($NiCl_2$) (available from Kishida Reagents Chemicals), 26 mg (0.23 mmol) of N,N,N',N'-tetramethylethylenediamine (TMEDA) (available from Kishida Reagents Chemicals), 79 mg (0.30 mmol) of triphenylphosphine ($PPh_3$) (available from Wako Pure Chem. Ind., Ltd.) and 11.0 g of tetrahydrofuran (available from Kanto Chemical Co., Ltd.), and the content of flask was heated under reflux of solvent for 30 minutes while being stirred. Then the reaction liquid was cooled to room temperature, and, 0.40 g (3.3 mmol) of phenylboronic acid ($PhB(OH)_2$) (available from Tokyo Chem. Ind. Co., Ltd.), 0.38 g (3.0 mmol) of p-chlorotoluene (available from Tokyo Chem. Ind. Co., Ltd.) and 1.24 g (9.0 mmol) of potassium carbonate ($K_2CO_3$) (available from Kishida Reagents Chemicals) were added to the reaction liquid. The mixture was heated under reflux of solvent for 12 hours while being stirred. After the completion of reaction, 5% aqueous HCl solution was added to the reaction liquid, and then the reaction liquid was phase-separated. The thus-obtained organic layer was washed with an aqueous saturated NaCl solution. Quantitative analysis of the organic layer by gas chromatography using n-dodecane (available from Tokyo Chem. Ind. Co., Ltd.) as internal standard substance revealed that the aimed 4-methylbiphenyl was produced in 77% yield (p-chlorotoluene basis). The reaction ingredients and results are shown in Table 1-1.

Example 2

A cross-coupling reaction was carried out by the same procedures as described in Example 1 except that 1.91 g (9.0 mmol) of potassium phosphate ($K_3PO_4$) (available from Wako Pure Chem. Ind., Ltd.) was used instead of 1.24 g (9.0 mmol) of potassium carbonate ($K_2CO_3$) with all other conditions remaining the same. The aimed 4-methylbiphenyl was produced in 74% yield (p-chlorotoluene basis). The reaction ingredients and results are shown in Table 1-1.

Example 3

A 50 ml flask flashed with nitrogen gas was charged with 23.3 mg (0.08 mmol) of nickel nitrate hexahydrate ($Ni(NO_3)_2 \cdot 6H_2O$) (available from Kishida Reagents Chemicals), 26 mg (0.23 mmol) of N,N,N',N'-tetramethylethylenediamine (TMEDA) (available from Kishida Reagents Chemicals), 79 mg (0.30 mmol) of triphenylphosphine ($PPh_3$) (available from Wako Pure Chem. Ind., Ltd.) and 11.0 g of tetrahydrofuran (available from Kanto Chemical Co., Ltd.), and the content of flask was heated under reflux of solvent for 30 minutes while being stirred. Then the reaction liquid was cooled to room temperature, and, 0.40 g (3.3 mmol) of phenylboronic acid ($PhB(OH)_2$) (available from Tokyo Chem. Ind., Ltd.), 0.38 g (3.0 mmol) of p-chlorotoluene (available from Tokyo Chem. Ind. Co., Ltd.) and 1.24 g (9.0 mmol) of potassium carbonate ($K_2CO_3$) (available from Kishida Reagents Chemicals) were added to the reaction liquid. The mixture was heated under reflux of solvent for 12 hours while being stirred. After the completion of reaction, 5% aqueous HCl solution was added to the reaction liquid, and then the reaction liquid was phase-separated. The thus-obtained organic layer was washed with an aqueous saturated NaCl solution. Quantitative analysis of the organic layer by gas chromatography using n-dodecane (available from Tokyo Chem. Ind. Co., Ltd.) as internal standard substance revealed that the aimed 4-methylbiphenyl was produced in 75% yield (p-chlorotoluene basis). The reaction ingredients and results are shown in Table 1-1.

Comparative Example 1

A cross-coupling reaction was carried out by the same procedures as described in Example 1 except that triphenylphosphine ($PPh_3$) was not used with all other conditions remaining the same. The aimed 4-methylbiphenyl was produced in 2% yield (p-chlorotoluene basis). The reaction ingredients and results are shown in Table 1-1.

Comparative Example 2

The same procedures as described in Example 1 were repeated except that N,N,N',N'-tetramethylethylenediamine (TMEDA) was not used with all other conditions remaining the same. The aimed 4-methylbiphenyl was not produced at all (yield: 0%). The reaction ingredients and results are shown in Table 1-1.

Comparative Example 3

A cross-coupling reaction was carried out by the same procedures as described in Example 1 except that triphenylphosphine ($PPh_3$) was not used, and the amount of N,N,N',N'-tetramethylethylenediamine (TMEDA) was changed from 26 mg (0.23 mol) to 62 mg (0.53 mmol) with all other conditions remaining the same. The aimed 4-methylbiphenyl was produced in 2% yield. The reaction ingredients and results are shown in Table 1-1.

Comparative Example 4

The same procedures as described in Example 1 were repeated except that N,N,N',N'-tetramethylethylenediamine (TMEDA) was not used and the amount of triphenylphosphine ($PPh_3$) was changed from 79 mg (0.30 mmol) to 139 mg (0.53 mmol) with all other conditions remaining the same. The aimed 4-methylbiphenyl was not produced at all (yield: 0%). The reaction ingredients and results are shown in Table 1-1.

Comparative Example 5

The same procedures as described in Example 1 were repeated except that 91.3 mg (0.30 mmol) of tri-o-tolylphosphine (available from STREM Chemicals, Inc.) was used instead of 79 mg (0.30 mmol) of triphenylphosphine ($PPh_3$) with all other conditions remaining the same. The aimed 4-methylbiphenyl was not produced at all (yield: 0%). The reaction ingredients and results are shown in Table 1-1.

Comparative Example 6

The same procedures as described in Example 1 were repeated except that 119.5 mg (0.30 mmol) of 1,2-bis(diphenylphosphino)ethane (available from STREM Chemicals, Inc.) was used instead of 79 mg (0.30 mmol) of triphenylphosphine ($PPh_3$) with all other conditions remaining the same. The aimed 4-methylbiphenyl was not produced at all (yield: 0%). The reaction ingredients and results are shown in Table 1-2.

Comparative Example 7

In this comparative example, cross-coupling reaction was carried out by substantially the same procedures as described in Tetrahedron, England, 1999, vol. 55, p 11889-11894.

A 50 ml flask flashed with nitrogen gas was charged with 9.7 mg (0.08 mmol) of anhydrous nickel chloride ($NiCl_2$) (available from Kishida Reagents Chemicals), 36 mg (0.23 mmol) of 2,2'-bipyridyl (BPY) (available from Aldrich Corporation) and 11.0 g of tetrahydrofuran (available from Kanto Chemical Co., Ltd.), and the content of flask was heated under reflux of solvent for 30 minutes while being stirred. Then the reaction liquid was cooled to room temperature, and, 0.40 g (3.3 mmol) of phenylboronic acid ($PhB(OH)_2$) (available from Tokyo Chem. Ind. Co., Ltd.), 0.38 g (3.0 mmol) of p-chlorotoluene (available from Tokyo Chem. Ind. Co., Ltd.) and 1.48 g (9.0 mmol) of sodium phosphate ($Na_3PO_4$) (available from Wako Pure Chem. Ind., Ltd.) were added to the reaction liquid. The mixture was heated under reflux of solvent for 12 hours while being stirred. After the completion of reaction, 5% aqueous HCl solution was added to the reaction liquid, and then the reaction liquid was phase-separated. The thus-obtained organic layer was washed with an aqueous saturated NaCl solution. Quantitative analysis of the organic layer by gas chromatography using n-dodecane (available from Tokyo Chem. Ind. Co., Ltd.) as internal standard substance revealed that the aimed 4-methylbiphenyl was produced in 41% yield (p-chlorotoluene basis). The reaction ingredients and results are shown in Table 1-2.

Comparative Example 8

The same procedures as described in Comparative Example 7 were repeated except that 1.24 g (9.0 mmol) of potassium carbonate ($K_2CO_3$) (available from Kishida Reagents Chemicals) was used instead of 1.48 g (9.0 mmol) of sodium phosphate ($Na_3PO_4$) with all other conditions remaining the same. The aimed 4-methylbiphenyl was not produced at all (yield: 0%). The reaction ingredients and results are shown in Table 1-2.

Comparative Example 9

A cross-coupling reaction was carried out by the same procedures as described in Comparative Example 7 except that 79 mg (0.30 mmol) of triphenylphosphine ($PPh_3$) (available from Wako Pure Chem. Ind., Ltd.) was charged together with the anhydrous nickel chloride ($NiCl_2$) and 2,2'-bipyridyl (BPY) in the flask, and that 1.91 g (9.0 mmol) of potassium phosphate ($K_3PO_4$) (available from Wako Pure Chem. Ind., Ltd.) was used instead of 1.48 g (9.0 mmol) of sodium phosphate ($Na_3PO_4$) with all other conditions remaining the same. The aimed 4-methylbiphenyl was produced in 35% yield (p-chlorotoluene basis). The reaction ingredients and results are shown in Table 1-2.

Comparative Example 10

A cross-coupling reaction was carried out by the same procedures as described in Comparative Example 9 except that 1.24 g (9.0 mmol) of potassium carbonate ($K_2CO_3$) (available from Kishida Reagents Chemicals) was used instead of 1.91 g (9.0 mmol) of potassium phosphate ($K_3PO_4$) (available from Wako Pure Chem. Ind., Ltd.) with all other conditions remaining the same. The aimed 4-methylbiphenyl was produced in 27% yield (p-chlorotoluene basis). The reaction ingredients and results are shown in Table 1-2.

Comparative Example 11

The same procedures as described in Example 3 were repeated except that triphenylphosphine ($PPh_3$) was not used with all other conditions remaining the same. The aimed 4-methylbiphenyl was not produced at all (yield: 0%). The reaction ingredients and results are shown in Table 1-2.

Comparative Example 12

A cross-coupling reaction was carried out by the same procedures as described in Example 3 except that N,N,N',N'-tetramethylethylenediamine (TMEDA) was not used with all other conditions remaining the same. The aimed 4-methylbiphenyl was produced in 34% yield (p-chlorotoluene basis). The reaction ingredients and results are shown in Table 1-2.

TABLE 1-1

| | Catalyst composition | | | | Solvent at reflux | Raw material | | Aimed product | Yield (%) |
|---|---|---|---|---|---|---|---|---|---|
| | Nickel | Amine | Phosphine | Base | | Boronic acid | Aromatic halide | | |
| Ex. 1 | NiCl$_2$ (0.08 mmol) | TMEDA (0.23 mmol) | PPh$_3$ (0.30 mmol) | K$_2$CO$_3$ (9.0 mmol) | THF | Ph-B(OH)$_2$ (3.3 mmol) | 4-Cl-C$_6$H$_4$-CH$_3$ (3.0 mmol) | 4-methylbiphenyl | 77 |
| Ex. 2 | NiCl$_2$ (0.08 mmol) | TMEDA (0.23 mmol) | PPh$_3$ (0.30 mmol) | K$_3$PO$_4$ (9.0 mmol) | " | Ph-B(OH)$_2$ (3.3 mmol) | 4-Cl-C$_6$H$_4$-CH$_3$ (3.0 mmol) | " | 74 |
| Ex. 3 | Ni(NO$_3$)$_2$ (0.08 mmol) | TMEDA (0.23 mmol) | PPh$_3$ (0.30 mmol) | K$_2$CO$_3$ (9.0 mmol) | " | Ph-B(OH)$_2$ (3.3 mmol) | 4-Cl-C$_6$H$_4$-CH$_3$ (3.0 mmol) | " | 75 |
| Com. Ex. 1 | NiCl$_2$ (0.08 mmol) | TMEDA (0.23 mmol) | — | K$_2$CO$_3$ (9.0 mmol) | " | Ph-B(OH)$_2$ (3.3 mmol) | 4-Cl-C$_6$H$_4$-CH$_3$ (3.0 mmol) | " | 2 |
| Com. Ex. 2 | NiCl$_2$ (0.08 mmol) | — | PPh$_3$ (0.30 mmol) | K$_2$CO$_3$ (9.0 mmol) | " | Ph-B(OH)$_2$ (3.3 mmol) | 4-Cl-C$_6$H$_4$-CH$_3$ (3.0 mmol) | " | 0 |

TABLE 1-1-continued

| | Catalyst composition | | | Base | Solvent at reflux | Raw material | | Aimed product | Yield (%) |
|---|---|---|---|---|---|---|---|---|---|
| | Nickel | Amine | Phosphine | | | Boronic acid | Aromatic halide | | |
| Com. Ex. 3 | NiCl$_2$ (0.08 mmol) | TMEDA (0.53 mmol) | — | K$_2$CO$_3$ (9.0 mmol) | at reflux |  Ph-B(OH)$_2$ (3.3 mmol) |  4-Cl-C$_6$H$_4$-CH$_3$ (3.0 mmol) | " | 2 |
| Com. Ex. 4 | NiCl$_2$ (0.08 mmol) | — | PPh$_3$ (0.53 mmol) | K$_2$CO$_3$ (9.0 mmol) | " | Ph-B(OH)$_2$ (3.3 mmol) | 4-Cl-C$_6$H$_4$-CH$_3$ (3.0 mmol) | " | 0 |
| Com. Ex. 5 | NiCl$_2$ (0.08 mmol) | TMEDA (0.23 mmol) |  P(o-tolyl)$_3$ (0.30 mmol) | K$_2$CO$_3$ (9.0 mmol) | " | 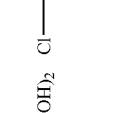 Ph-B(OH)$_2$ (3.3 mmol) | 4-Cl-C$_6$H$_4$-CH$_3$ (3.0 mmol) | " | 0 |

TABLE 1-2

| | Catalyst composition | | | Base | Solvent at reflux | Raw material | | Aimed product | Yield (%) |
|---|---|---|---|---|---|---|---|---|---|
| | Nickel | Amine | Phosphine | | | Boronic acid | Aromatic halide | | |
| Com. Ex. 6 | NiCl$_2$ (0.08 mmol) | TMEDA (0.23 mmol) | Ph$_2$P⌒PPh$_2$ (0.30 mmol) | K$_2$CO$_3$ (9.0 mmol) | THF |  B(OH)$_2$ (3.3 mmol) |  CH$_3$, Cl (3.0 mmol) |  CH$_3$ | 0 |
| Com. Ex. 7 | NiCl$_2$ (0.08 mmol) | BPY (0.23 mmol) | — | Na$_3$PO$_4$ (9.0 mmol) | " | 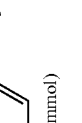 B(OH)$_2$ (3.3 mmol) |  CH$_3$, Cl (3.0 mmol) | " | 41 |
| Com. Ex. 8 | NiCl$_2$ (0.08 mmol) | BPY (0.23 mmol) | — | K$_2$CO$_3$ (9.0 mmol) | " |  B(OH)$_2$ (3.3 mmol) |  CH$_3$, Cl (3.0 mmol) | " | 0 |
| Com. Ex. 9 | NiCl$_2$ (0.08 mmol) | BPY (0.23 mmol) | PPh$_3$ (0.30 mmol) | K$_3$PO$_4$ (9.0 mmol) | " |  B(OH)$_2$ (3.3 mmol) |  CH$_3$, Cl (3.0 mmol) | " | 35 |
| Com. Ex. 10 | NiCl$_2$ (0.08 mmol) | BPY (0.23 mmol) | PPh$_3$ (0.30 mmol) | K$_2$CO$_3$ (9.0 mmol) | " |  B(OH)$_2$ (3.3 mmol) |  CH$_3$, Cl (3.0 mmol) | " | 27 |
| Com. Ex. 11 | Ni(NO$_3$)$_2$ (0.08 mmol) | TMEDA (0.23 mmol) | — | K$_2$CO$_3$ (9.0 mmol) | " |  B(OH)$_2$ (3.3 mmol) |  CH$_3$, Cl (3.0 mmol) | " | 0 |
| Com. Ex. 12 | Ni(NO$_3$)$_2$ (0.08 mmol) | — | PPh$_3$ (0.30 mmol) | K$_2$CO$_3$ (9.0 mmol) | " | 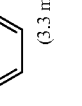 B(OH)$_2$ (3.3 mmol) | 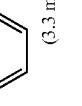 CH$_3$, Cl (3.0 mmol) | " | 34 |

Examples 4 to 11

A cross-coupling reactions were carried out by the same procedures as described in Example 1 except that 3.3 mmol of each of the aromatic boronic acids and 3.0 mmol of each of the aromatic halides, which are shown in Table 2 below, were used instead of 0.40 g (3.3 mmol) of phenylboronic acid (PhB(OH)$_2$) and 0.38 g (3.0 mmol) of p-chlorotoluene with all other conditions remaining the same. The reaction ingredients and results are shown In Table 2.

Example 12

A cross-coupling reaction was carried out by the same procedures as described in Example 1 except that 30 mg (0.23 mmol) of N,N,N',N'-tetramethylpropylenediamine (available from Aldrich Corporation) was used instead of 26 mg (0.23 mmol) of N,N,N',N'-tetramethylethylenediamine (TMEDA) with all other conditions remaining the same. The aimed 4-methylbiphenyl was produced in 77% yield (p-chlorotoluene basis). The reaction ingredients and results are shown in Table 2.

TABLE 2

| | Catalyst composition | | | Base | Solvent at reflux | Raw material | | Aimed product | Yield (%) |
|---|---|---|---|---|---|---|---|---|---|
| | Nickel | Amine | Phosphine | | | Boronic acid | Aromatic halide | | |
| Ex. 4 | NiCl$_2$ (0.08 mmol) | TMEDA (0.23 mmol) | PPh$_3$ (0.30 mmol) | K$_2$CO$_3$ (9.0 mmol) | THF | Ph-B(OH)$_2$ (3.3 mmol) | Ph-Cl (3.0 mmol) | biphenyl | 81 |
| Ex. 5 | NiCl$_2$ (0.08 mmol) | TMEDA (0.23 mmol) | PPh$_3$ (0.30 mmol) | K$_2$CO$_3$ (9.0 mmol) | " | Ph-B(OH)$_2$ (3.3 mmol) | 4-CF$_3$-C$_6$H$_4$-Cl (3.0 mmol) | 4-CF$_3$-biphenyl | 87 |
| Ex. 6 | NiCl$_2$ (0.08 mmol) | TMEDA (0.23 mmol) | PPh$_3$ (0.30 mmol) | K$_2$CO$_3$ (9.0 mmol) | " | Ph-B(OH)$_2$ (3.3 mmol) | 4-CN-C$_6$H$_4$-Cl (3.0 mmol) | 4-CN-biphenyl | 88 |
| Ex. 7 | NiCl$_2$ (0.08 mmol) | TMEDA (0.23 mmol) | PPh$_3$ (0.30 mmol) | K$_2$CO$_3$ (9.0 mmol) | " | Ph-B(1,3-propanediol ester) (3.3 mmol) | 4-CN-C$_6$H$_4$-Cl (3.0 mmol) | " | 85 |
| Ex. 8 | NiCl$_2$ (0.08 mmol) | TMEDA (0.23 mmol) | PPh$_3$ (0.30 mmol) | K$_2$CO$_3$ (9.0 mmol) | " | 4-MeO-C$_6$H$_4$-B(OH)$_2$ (3.3 mmol) | 4-CH$_3$-C$_6$H$_4$-Cl (3.0 mmol) | 4-MeO-4'-CH$_3$-biphenyl | 80 |

TABLE 2-continued

| | Catalyst composition | | | | | Raw material | | | |
|---|---|---|---|---|---|---|---|---|---|
| | Nickel | Amine | Phosphine | Base | Solvent at reflux | Boronic acid | Aromatic halide | Aimed product | Yield (%) |
| Ex. 9 | NiCl$_2$ (0.08 mmol) | TMEDA (0.23 mmol) | PPh$_3$ (0.30 mmol) | K$_2$CO$_3$ (9.0 mmol) | " | MeO–C$_6$H$_4$–B(OH)$_2$ (3.3 mmol) | C$_6$H$_5$–Cl (3.0 mmol) | MeO–C$_6$H$_4$–C$_6$H$_5$ | 89 |
| Ex. 10 | NiCl$_2$ (0.08 mmol) | TMEDA (0.23 mmol) | PPh$_3$ (0.30 mmol) | K$_2$CO$_3$ (9.0 mmol) | " | MeO–C$_6$H$_4$–B(OH)$_2$ (3.3 mmol) | NC–C$_6$H$_4$–Cl (3.0 mmol) | MeO–C$_6$H$_4$–C$_6$H$_4$–CN | 91 |
| Ex. 11 | NiCl$_2$ (0.08 mmol) | TMEDA (0.23 mmol) | PPh$_3$ (0.30 mmol) | K$_2$CO$_3$ (9.0 mmol) | " | F–C$_6$H$_4$–B(OH)$_2$ (3.3 mmol) | NC–C$_6$H$_4$–Cl (3.0 mmol) | F–C$_6$H$_4$–C$_6$H$_4$–CN | 83 |
| Ex. 12 | NiCl$_2$ (0.08 mmol) | Me$_2$N(CH$_2$)$_3$NMe$_2$ (0.23 mmol) | PPh$_3$ (0.30 mmol) | K$_2$CO$_3$ (9.0 mmol) | " | C$_6$H$_5$–B(OH)$_2$ (3.3 mmol) | CH$_3$–C$_6$H$_4$–Cl (3.0 mmol) | CH$_3$–C$_6$H$_4$–C$_6$H$_5$ | 77 |

Example 13

A 50 ml flask flashed with nitrogen gas was charged with 52.3 mg (0.08 mmol) of dichlorobis(triphenylphosphine) nickel ($NiCl_2(PPh_3)_2$) (available from Aldrich Corporation), 26 mg (0.23 mmol) of N,N,N',N'-tetramethylethylenediamine (TMEDA) (available from Kishida Reagents Chemicals), 39 mg (0.15 mmol) of triphenylphosphine ($PPh_3$) (available from Wako Pure Chem. Ind., Ltd.) and 11.0 g of tetrahydrofuran (available from Kanto Chemical Co., Ltd.), and the content of flask was heated under reflux of solvent for 30 minutes while being stirred. Then the reaction liquid was cooled to room temperature, and, 0.40 g (3.3 mmol) of phenylboronic acid ($PhB(OH)_2$) (available from Tokyo Chem. Ind. Co., Ltd.), 0.38 g (3.0 mmol) of p-chlorotoluene (available from Tokyo Chem. Ind. Co., Ltd.) and 1.24 g (9.0 mmol) of potassium carbonate ($K_2CO_3$) (available from Kishida Reagents Chemicals) were added to the reaction liquid. The mixture was heated under reflux of solvent for 12 hours while being stirred. After the completion of reaction, 5% aqueous HCl solution was added to the reaction liquid, and then the reaction liquid was phase-separated. The thus-obtained organic layer was washed with an aqueous saturated NaCl solution. Quantitative analysis of the organic layer by gas chromatography using n-dodecane (available from Tokyo Chem. Ind. Co., Ltd.) as internal standard substance revealed that the aimed 4-methylbiphenyl was produced in 75% yield (p-chlorotoluene basis).

Example 14

Preparation of Nickel Salt-Amine Complex

A 200 ml flask flashed with nitrogen gas was charged with 13.0 g (0.10 mol) of anhydrous nickel chloride ($NiCl_2$) (available from Kishida Reagents Chemicals), 13.9 g (0.12 mol) of N,N,N',N'-tetramethylethylenediamine (TMEDA) (available from Kishida Reagents Chemicals) and 50.0 g of dehydrated methanol (available from Kanto Chemical Co., Ltd.), and the content of flask was heated under reflux of solvent in a nitrogen atmosphere for 1 hour. After the completion of reaction, the reaction liquid was cooled to room temperature. Then the thus-precipitated solid was filtered, and dried in vacuo to give 19.7 g of a greenish yellow solid. Elementary analysis of the solid revealed that it was a complex of nickel chloride with TMEDA (mol ratio: 1:1) (yield: 80%).

Elementary analysis: Nickel chloride-TMEDA [1:1] complex

Calculated: C=29.3%, H=6.6%, Cl=28.9%, N=11.4%, Ni=23.9%

Found: C=29.5%, H=6.4%, Cl=28.8%, N=11.4%, Ni=23.7%

Synthesis of Cross-Coupled Compound

A 50 ml flask flashed with nitrogen gas was charged with 7.37 mg (0.03 mmol) of nickel chloride-TMEDA [1:1] complex prepared by the above-mentioned procedures, 24 mg (0.09 mmol) of triphenylphosphine ($PPh_3$) (available from Wako Pure Chem. Ind. Ltd.) and 11.0 g of tetrahydrofuran (available from Kanto Chemical Co., Ltd.). Further, 0.44 g (3.6 mmol) of phenylboronic acid ($PhB(OH)_2$) (available from Tokyo Chem. Ind. Co., Ltd.), 0.38 g (3.0 mmol) of p-chlorotoluene (available from Tokyo Chem. Ind. Co., Ltd.) and 1.24 g (9.0 mmol) of potassium carbonate ($K_2CO_3$) (available from Kishida Reagents Chemicals) were added to the content of flask, and the mixture was heated under reflux of solvent for 12 hours while being stirred. After the completion of reaction, 5% aqueous HCl solution was added to the reaction liquid, and then the reaction liquid was phase-separated. The thus-obtained organic layer was washed with an aqueous saturated NaCl solution. Quantitative analysis of the organic layer by gas chromatography using n-dodecane (available from Tokyo Chem. Ind. Co., Ltd.) as internal standard substance revealed that the aimed 4-methylbiphenyl was produced in 84% yield (p-chlorotoluene basis). The reaction ingredients and results are shown in Table 3-1.

Example 15

A cross-coupling reaction was carried out by the same procedures as described in Example 14 except that 5.0 g of dioxane (available from Kanto Chemical Co., Ltd.) was used instead of 11.0 g of tetrahydrofuran with all other conditions remaining the same. The aimed 4-methylbiphenyl was produced in 95% yield (p-chlorotoluene basis). The reaction ingredients and results are shown in Table 3-1.

Example 16

A 50 ml flask flashed with nitrogen gas was charged with 7.37 mg (0.03 mmol) of nickel chloride-TMEDA [1:1] complex prepared in Example 14, and 5.0 g of 1,4-dioxane (available from Kanto Chemical Co., Ltd.), and the content of flask was maintained at 80° C. for 0.5 hour to give a purple reaction liquid.

Separately, a 50 ml flask flashed with nitrogen gas was charged with 0.44 g (3.6 mmol) of phenylboronic acid ($PhB(OH)_2$) (available from Tokyo Chem. Ind. Co., Ltd.), 0.38 g (3.0 mmol) of p-chlorotoluene (available from Tokyo Chem. Ind. Co., Ltd.), 24 mg (0.09 mmol) of triphenylphosphine ($PPh_3$) (available from Wako Pure Chem. Ind., Ltd.), 1.24 g (9.0 mmol) of potassium carbonate ($K_2CO_3$) (available from Kishida Reagents Chemicals) and 10.0 g of 1,4-dioxane (available from Kanto Chemical Co., Ltd.). The content of flask was heated to a solvent-reflux temperature, and the above-mentioned purple reaction liquid (nickel chloride-TMEDA [1:1] complex/dioxane liquid) was added to the heated content of the flask. The mixture was maintained under reflux of solvent for 12 hours while being stirred. After the completion of reaction, 5% aqueous HCl solution was added to the reaction liquid, and then the reaction liquid was phase-separated. The thus-obtained organic layer was washed with an aqueous saturated NaCl solution. Quantitative analysis of the organic layer by gas chromatography using n-dodecane (available from Tokyo Chem. Ind. Co., Ltd.) as internal standard substance revealed that the aimed 4-methylbiphenyl was produced in 94% yield (p-chlorotoluene basis).

Example 17

A nickel chloride-N,N,N',N'-tetramethylproylenediamine [1:1] complex was prepared by a procedure similar to that described for the preparation of nickel chloride-TMEDA [1:1] complex in Example 14.

A cross-coupling reaction was carried out by the same procedures as described in Example 14 except that 7.79 mg (0.03 mmol) of the nickel chloride-N,N,N',N'-tetramethylpropylene diamine [1:1] complex was used instead of 7.37 mg (0.03 mmol) of the nickel chloride-TMEDA [1:1] complex with all other conditions remaining the same. The aimed 4-methylbiphenyl was produced in 61% yield (p-chlorotoluene basis). The reaction ingredients and results are shown in Table 3-1.

Example 18

A nickel bromide-N,N,N',N'-tetramethylethylenediamine (TMEDA) [1:1] complex was prepared by a procedure similar to that described for the preparation of nickel chloride-TMEDA [1:1] complex in Example 14.

A cross-coupling reaction was carried out by the same procedures as described in Example 14 except that 10.0 mg (0.03 mmol) of the nickel bromide-TMEDA [1:1] complex was used instead of 7.37 mg (0.03 mmol) of the nickel chloride-TMEDA [1:1] complex with all other conditions remaining the same. The aimed 4-methylbiphenyl was produced in 82% yield (p-chlorotoluene basis). The reaction ingredients and results are shown in Table 3-1.

Example 19

A 50 ml flask flashed with nitrogen gas was charged with 7.37 mg (0.03 mmol) of the nickel chloride-TMEDA [1:1] complex prepared in Example 14, 24 mg (0.09 mmol) of triphenylphosphine (PPh$_3$) (available from Wako Pure Chem. Ind., Ltd.) and 10.0 g of tetrahydrofuran (available from Kanto Chemical Co., Ltd.). Further, 0.63 g (1.2 mmol) of tris(4-t-butoxyphenyl)boroxine, 0.41 g (3.0 mmol) of p-chlorobenzonitrile (available from Tokyo Chem. Ind. Co., Ltd.) and 1.24 g (9.0 mmol) of potassium carbonate (K$_2$CO$_3$) (available from Kishida Reagents Chemicals) were added to the content of flask, and the mixture was heated under reflux of solvent for 12 hours while being stirred. After the completion of reaction, 5% aqueous HCl solution was added to the reaction liquid, and then the reaction liquid was phase-separated. The thus-obtained organic layer was washed with an aqueous saturated NaCl solution. Quantitative analysis of the organic layer by gas chromatography using n-dodecane (available from Tokyo Chem. Ind. Co., Ltd.) as internal standard substance revealed that the aimed 4-t-butoxy-4'-cyano-biphenyl was produced in 96% yield (p-chlorobenzonitrile basis). The reaction ingredients and results are shown in Table 3-1.

Example 20

A cross-coupling reaction was carried out by the same procedures as described in Example 15 except that 0.51 g (3.0 mmol) of p-bromotoluene (available from Tokyo Chem. Ind. Co., Ltd.) was used instead of 0.38 g (3.0 mmol) of p-chlorotoluene with all other conditions remaining the same. The aimed 4-methylbiphenyl was produced in 89% yield (p-bromotoluene basis). The reaction ingredients and results are shown in Table 3-1.

Example 21

A cross-coupling reaction was carried out by the same procedures as described in Example 15 except that 0.65 g (3.0 mmol) of p-iodotoluene (available from Tokyo Chem. Ind. Co., Ltd.) was used instead of 0.38 g (3.0 mmol) of p-chlorotoluene with all other conditions remaining the same. The aimed 4-methylbiphenyl was produced in 85% yield (p-iodotoluene basis). The reaction ingredients and results are shown in Table 3-2.

Example 22

A cross-coupling reaction was carried out by the same procedures as described in Example 15 except that 0.55 g (3.0 mmol) of trans-β-bromostyrene was used instead of 0.38 g (3.0 mmol) of p-chlorotoluene with all other conditions remaining the same. The aimed trans-stilbene was produced in 59% yield (trans β-bromostyrene basis). The reaction ingredients and results are shown in Table 3-2.

Example 23

A 50 ml flask flashed with nitrogen gas was charged with 7.37 mg (0.03 mmol) of the nickel chloride-TMEDA [1:1] complex prepared in Example 14, 24 mg (0.09 mmol) of triphenylphosphine (PPh$_3$) (available from Wako Pure Chem. Ind., Ltd.) and 10.0 g of 1,4-dioxane (available from Kanto Chemical Co., Ltd.). Further, 0.58 g (3.6 mmol) of trans-2-(4-methylphenyl)vinylboronic acid (available from Aldrich Corporation), 0.47 g (3.0 mmol) of bromobenzene (available from Kanto Chemical Co., Ltd.) and 1.24 g (9.0 mmol) of potassium carbonate (K$_2$CO$_3$) (available from Kishida Reagents Chemicals) were added to the content of flask, and the mixture was heated under reflux of solvent for 12 hours while being stirred. After the completion of reaction, 5% aqueous HCl solution was added to the reaction liquid, and then the reaction liquid was phase-separated. The thus-obtained organic layer was washed with an aqueous saturated NaCl solution. Quantitative analysis of the organic layer by gas chromatography using n-dodecane (available from Tokyo Chem. Ind. Co., Ltd.) as internal standard substance revealed that the aimed trans-β-(4-methylphenyl) styrene was produced in 63% yield (bromobenzene basis). The reaction ingredients and results are shown in Table 3-2.

Example 24

A cross-coupling reaction was carried out by the same procedures as described in Example 23 except that 0.61 g (3.0 mmol) of Iodobenzene (available from Tokyo Chem. Ind. Co., Ltd.) was used instead of 0.47 g (3.0 mmol) of bromobenzene with all other conditions remaining the same. The aimed trans-β-(4-methylphenyl)styrene was produced in 61% yield (iodobenzene basis), The reaction ingredients and results are shown in Table 3-2.

Example 25

A 50 ml flask flashed with nitrogen gas was charged with 7.37 mg (0.03 mmol) of the nickel chloride-TMEDA [1:1] complex prepared in Example 14, 24 mg (0.09 mmol) of triphenylphosphine (PPh$_3$) (available from Wako Pure Chem. Ind., Ltd.) and 10.0 g of 1,4-dioxane (available from Kanto Chemical Co., Ltd.). Further, 0.53 g (3.6 mmol) of trans-2-phenylvinylboronic acid (available from Aldrich Corporation), 0.47 g (3.0 mmol) of bromobenzene (available from Kanto Chemical Co., Ltd.) and 1.91 g (9.0 mmol) of potassium phosphate (K$_3$PO$_4$) (available from Wako Pure Chem. Ind., Ltd.) were added to the content of flask, and the mixture was heated under reflux of solvent for 12 hours while being stirred. After the completion of reaction, 5% aqueous HCl solution was added to the reaction liquid, and then the reaction liquid was phase-separated. The thus-obtained organic layer was washed with an aqueous saturated NaCl solution. Quantitative analysis of the organic layer by gas chromatography using n-dodecane (available from Tokyo Chem. Ind. Co., Ltd.) as internal standard substance revealed that the aimed trans-stilbene was produced in 91% yield (bromobenzene basis). The reaction ingredients and results are shown in Table 3-2.

Example 26

A cross-coupling reaction was carried out by the same procedures as described in Example 25 except that 0.61 g (3.0 mmol) of iodobenzene (available from Tokyo Chem. Ind. Co., Ltd.) was used instead of 0.47 g (3.0 mmol) of bromobenzene with all other conditions remaining the same. The aimed trans-stilbene was produced in 86% yield (Iodobenzene basis). The reaction ingredients and results are shown in Table 3-2.

Example 27

A cross-coupling reaction was carried out by the same procedures as described in Example 25 except that 0.55 g (3.0 mmol) of trans-β-bromostyrene was used instead of 0.47 g (3.0 mmol) of bromobenzene with all other conditions remaining the same. The aimed trans-trans-1,4-butadiene was produced in 59% yield (trans-β-bromostyrene basis). The reaction ingredients and results are shown in Table 3-2.

INDUSTRIAL APPLICABILITY

The catalyst composition according to the present invention has high activity for a cross-coupling reaction such as Suzuki cross-coupling reaction.

By the process using the catalyst composition according to the present invention, a cross-coupled compound can be produced with an enhanced efficiency in a high yield. Even when a less expensive base such as carbonate salts is used, a cross-coupled compound can be produced in a high yield.

The cross-coupled compound produced includes, for example, 4-t-butoxy-4'-cyanobiphenyl which is an intermediate for 4-hydroxy-4'-cyanobiphenyl as used for a liquid crystal material.

TABLE 3-1

| | Catalyst composition | | | | Raw material | | | |
|---|---|---|---|---|---|---|---|---|
| | Nickel-amine complex | Phosphine | Base | Solvent at reflux | Boronic acid | Aromatic halide | Aimed product | Yield (%) |
| Ex. 14 | NiCl$_2$(TMEDA) (0.03 mmol) | PPh$_3$ (0.09 mmol) | K$_2$CO$_3$ (9.0 mmol) | THF | 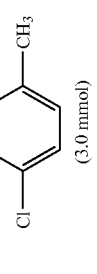 PhB(OH)$_2$ (3.6 mmol) |  4-Cl-C$_6$H$_4$-CH$_3$ (3.0 mmol) | 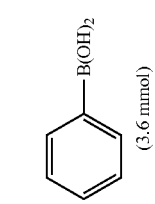 4-methylbiphenyl | 84 |
| Ex. 15 | NiCl$_2$(TMEDA) (0.03 mmol) | PPh$_3$ (0.09 mmol) | K$_2$CO$_3$ (9.0 mmol) | Dioxane | 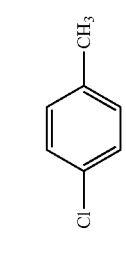 (3.6 mmol) |  (3.0 mmol) | " | 95 |
| Ex. 17 |  (0.03 mmol) | PPh$_3$ (0.09 mmol) | K$_2$CO$_3$ (9.0 mmol) | THF | 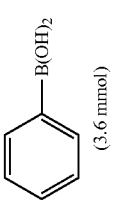 (3.6 mmol) | 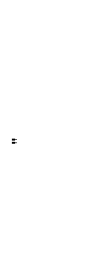 (3.0 mmol) | " | 61 |
| Ex. 18 | 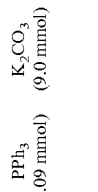 (0.03 mmol) | PPh$_3$ (0.09 mmol) | K$_2$CO$_3$ (9.0 mmol) | " | 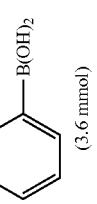 (3.6 mmol) | 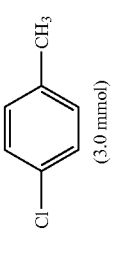 (3.0 mmol) | " | 82 |

TABLE 3-1-continued
| | Catalyst composition | | | | Raw material | | Yield |
| --- | --- | --- | --- | --- | --- | --- | --- |
| | Nickel-amine complex | Phosphine | Base | Solvent | Boronic acid | Aromatic halide | Aimed product | (%) |
| Ex. 19 | NiCl$_2$(TMEDA) (0.03 mmol) | PPh$_3$ (0.09 mmol) | K$_2$CO$_3$ (9.0 mmol) | at reflux " |  (1.2 mmol) |  (3.0 mmol) |  | 96 |
| Ex. 20 | NiCl$_2$(TMEDA) (0.03 mmol) | PPh$_3$ (0.09 mmol) | K$_2$CO$_3$ (9.0 mmol) | Dioxane |  (3.6 mmol) |  (3.0 mmol) |  | 89 |

TABLE 3-2

| | Catalyst composition | | | Solvent at reflux | Raw material | | | Yield (%) |
|---|---|---|---|---|---|---|---|---|
| | Nickel-amine complex | Phosphine | Base | | Boronic acid | Halide | Aimed product | |
| Ex. 21 | NiCl$_2$(TMEDA) (0.03 mmol) | PPh$_3$ (0.09 mmol) | K$_2$CO$_3$ (9.0 mmol) | Dioxane | PhB(OH)$_2$ (3.6 mmol) | 4-iodotoluene (3.0 mmol) | 4-methylbiphenyl (3.0 mmol) | 85 |
| Ex. 22 | NiCl$_2$(TMEDA) (0.03 mmol) | PPh$_3$ (0.09 mmol) | K$_2$CO$_3$ (9.0 mmol) | " | PhB(OH)$_2$ (3.6 mmol) | (E)-β-bromostyrene (3.0 mmol) | (E)-stilbene | 59 |
| Ex. 23 | NiCl$_2$(TMEDA) (0.03 mmol) | PPh$_3$ (0.09 mmol) | K$_2$CO$_3$ (9.0 mmol) | " | p-Me-C$_6$H$_4$-CH=CH-B(OH)$_2$ (3.6 mmol) | PhBr (3.0 mmol) | p-Me-C$_6$H$_4$-CH=CH-Ph | 63 |
| Ex. 24 | NiCl$_2$(TMEDA) (0.03 mmol) | PPh$_3$ (0.09 mmol) | K$_2$CO$_3$ (9.0 mmol) | " | p-Me-C$_6$H$_4$-CH=CH-B(OH)$_2$ (3.6 mmol) | PhI (3.0 mmol) | " | 61 |

TABLE 3-2-continued

| | Catalyst composition | | | Solvent | Raw material | | Aimed product | Yield (%) |
|---|---|---|---|---|---|---|---|---|
| | Nickel-amine complex | Phosphine | Base | | Boronic acid | Halide | | |
| Ex. 25 | NiCl$_2$(TMEDA) (0.03 mmol) | PPh$_3$ (0.09 mmol) | K$_3$PO$_4$ (9.0 mmol) | at reflux | Ph–CH=CH–B(OH)$_2$ (3.6 mmol) | Ph–Br (3.0 mmol) | Ph–CH=CH–Pr | 91 |
| Ex. 26 | NiCl$_2$(TMEDA) (0.03 mmol) | PPh$_3$ (0.09 mmol) | K$_3$PO$_4$ (9.0 mmol) | " | Ph–CH=CH–B(OH)$_2$ (3.6 mmol) | Ph–I (3.0 mmol) | " | 86 |
| Ex. 27 | NiCl$_2$(TMEDA) (0.03 mmol) | PPh$_3$ (0.09 mmol) | K$_3$PO$_4$ (9.0 mmol) | " | Ph–CH=CH–B(OH)$_2$ (3.6 mmol) | Ph–CH=CH–Br (3.0 mmol) | Ph–CH=CH–CH=CH–Ph | 59 |

What is claimed is:

1. A process for producing a cross-coupled compound represented by the following formula (4):

wherein $R^5$ and $R^6$ may be the same or different and represent a substituted or unsubstituted linear, branched or cyclic alkyl group, a substituted or unsubstituted aryl group, a substituted or unsubstituted heteroaryl group, or a substituted or unsubstituted linear, branched or cyclic alkenyl group; which comprises allowing a boron-containing compound represented by the following formula (2) to react with a compound represented by the following formula (3):

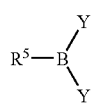

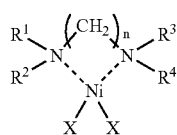

wherein $R^5$ and $R^6$ are as defined above; Y may be the same or different and each Y represents a hydroxyl group or an alkoxy group, provided that, when each Y is a hydroxyl group, three boron-containing compounds may be dehydration-condensed to form a trimer anhydride, and that, when two Y are an alkoxy group, the two Y may be bonded together to form a ring; and Z represents a halogen atom, a methanesulfonate group or a trifluoromethane-sulfonate group; in the presence of a base and a catalyst composition for a cross-coupling reaction comprising a complex of a nickel salt with an amine compound, represented by the following formula (1), and triphenylphosphine (1)

wherein $R^1$ through $R^4$ may be the same or different and represent a substituted or unsubstituted linear, branched or cyclic alkyl group, a substituted or unsubstituted aryl group, a substituted or unsubstituted heteroaryl group, or a substituted or unsubstituted linear, branched or cyclic alkenyl group; n is an integer of 1 to 6; and X may be the same or different and each X represents a halogen atom, a hydroxyl group, a nitrate group or an acetate group.

2. The process for producing a cross-coupled compound according to claim 1, wherein the base is a carbonic acid salt compound.

3. The process for producing a cross-coupled compound according to claim 2, wherein the boron-containing compound of formula (2) is an aromatic boron-containing compound represented by the following formula (5) or an alkenyl boron-containing compound represented by the following formula (6);

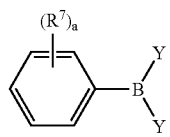

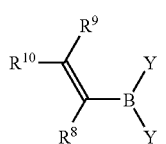

wherein $R^7$ through $R^{10}$ may be the same or different and represent a hydrogen atom, a halogen atom, a substituted or unsubstituted linear, branched or cyclic alkyl group, a substituted or unsubstituted aryl group, a substituted or unsubstituted heteroaryl group, or a substituted or unsubstituted linear, branched or cyclic alkenyl group, a hydroxyl group, an alkoxy group, an amino group, a cyano group, a carbonyl group, a carboxyl group or an ester group; provided that two $R^7$s bonded to two adjacent carbon atoms on the benzene ring in the formula (5) may be bonded together to form a condensed ring with the benzene ring, and two adjacent $R^8$ and $R^{10}$ on the alkenyl group in the formula (6) may be bonded together to form a ring, and $R^9$ and $R^{10}$ bonded to the same carbon atom on the alkenyl group in the formula (6) may be bonded together to form a ring; a is an integer of 1 to 5; and Y may be the same or different and each Y represents a hydroxyl group or an alkoxy group.

4. The process for producing a cross-coupled compound according to claim 3, wherein the compound of the formula (3) is an aromatic compound represented by the following formula (7) or an alkanyl compound represented by the following formula (8):

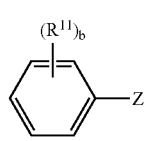

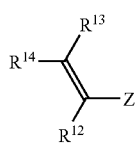

wherein $R^{11}$ through $R^{14}$ may be the same or different and represent a hydrogen atom, a halogen atom, a substituted or unsubstituted linear, branched or cyclic alkyl group, a substituted or unsubstituted aryl group, a substituted or unsubstituted heteroaryl group, or a substituted or unsubstituted linear, branched or cyclic alkenyl group, a hydroxyl group, an alkoxy group, an amino group, a cyano group, a carbonyl group, a carboxyl group or an ester group; provided that two $R^{11}$s bonded to two adjacent carbon atoms on the benzene ring in the formula (7) may be bonded together to form a condensed ring with the benzene ring, and two adjacent $R^{12}$ and $R^{14}$ on the alkenyl group in the formula (8) may be bonded together to form a ring, and $R^{13}$ and $R^{14}$ bonded to the same carbon atom on the alkenyl group in the formula (8) may be bonded together to form a ring; b is an integer of 1 to 5; and Z represents a halogen atom, a methanesulfonate group or a trifluoromethanesulfonate group.

5. The process for producing a cross-coupled compound according to claim 1, wherein the boron-containing compound of formula (2) is an aromatic boron-containing compound represented by the following formula (5) or an alkenyl boron-containing compound represented by the following formula (6):

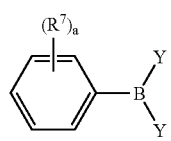

(5)

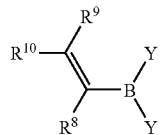

(6)

wherein $R^7$ through $R^{10}$ may be the same or different and represent a hydrogen atom, a halogen atom, a substituted or unsubstituted linear, branched or cyclic alkyl group, a substituted or unsubstituted aryl group, a substituted or unsubstituted heteroaryl group, or a substituted or unsubstituted linear, branched or cyclic alkenyl group, a hydroxyl group, an alkoxy group, an amino group, a cyano group, a carbonyl group, a carboxyl group or an ester group; provided that two $R^7$s bonded to two adjacent carbon atoms on the benzene ring in the formula (5) may be bonded together to form a condensed ring with the benzene ring, and two adjacent $R^8$ and $R^{10}$ on the alkenyl group in the formula (6) may be bonded together to form a ring, and $R^9$ $R^{10}$ bonded to the same carbon atom on the alkenyl group in the formula (6) may be bonded together to form a ring; a is an integer of 1 to 5; and Y may be the same or different and each Y represents a hydroxyl group or an alkoxy group.

6. The process for producing a cross-coupled compound according to claim 5, wherein the compound of the formula (3) is an aromatic compound represented by the following formula (7) or an alkenyl compound represented by the following formula (8):

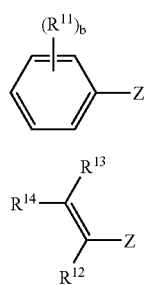

(7)

(8)

wherein $R^{11}$ through $R^{14}$ may be the same or different and represent a hydrogen atom, a halogen atom, a substituted or unsubstituted linear, branched or cyclic alkyl group, a substituted or unsubstituted aryl group, a substituted or unsubstituted heteroaryl group, or a substituted or unsubstituted linear, branched or cyclic alkenyl group, a hydroxyl group, an alkoxy group, an amino group, a cyano group, a carbonyl group, a carboxyl group or an ester group; provided that two $R^{11}$s bonded to two adjacent carbon atoms on the benzene ring in the formula (7) may be bonded together to form a condensed ring with the benzene ring, and two adjacent $R^{12}$ and $R^{14}$ on the alkenyl group in the formula (8) may be bonded together to form a ring, and $R^{13}$ and $R^{14}$ bonded to the same carbon atom on the alkenyl group in the formula (8) may be bonded together to form a ring; b is an integer of 1 to 5; and Z represents a halogen atom, a methanesulfonate group or a trifluoromethanesulfonate group.

7. The process for producing a cross-coupled compound according to claim 1, wherein the compound of the formula (3) is an aromatic compound represented by the following formula (7) or an alkenyl compound represented by the following formula (8):

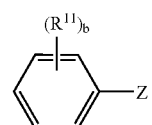

(7)

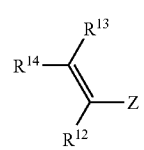

(8)

wherein $R^{11}$ through $R^{14}$ may be the same or different and represent a hydrogen atom, a halogen atom, a substituted or unsubstituted linear, branched or cyclic alkyl group, a substituted or unsubstituted aryl group, a substituted or unsubstituted heteroaryl group, or a substituted or unsubstituted linear, branched or cyclic alkenyl group, a hydroxyl group, an alkoxy group, an amino group, a cyano group, a carbonyl group, a carboxyl group or an ester group; provided that two $R^{11}$s bonded to two adjacent carbon atoms on the benzene ring in the formula (7) may be bonded together to form a condensed ring with the benzene ring, and two adjacent $R^{12}$ and $R^{14}$ on the alkenyl group in the formula (8) may be bonded together to form a ring, and $R^{13}$ and $R^{14}$ bonded to the same carbon atom on the alkenyl group in the formula (8) may be bonded together to form a ring; b is an integer of 1 to 5; and Z represents a halogen atom, a methanesulfonate group or a trifluoromethanesulfonate group.

8. The process for producing a cross-coupled compound according to claim 2, wherein the compound of the formula (3) is an aromatic compound represented by the following formula (7) or an alkenyl compound represented by the following formula (8):

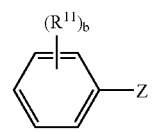

(7)

-continued

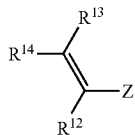

(8)

wherein $R^{11}$ through $R^{14}$ may be the same or different and represent a hydrogen atom, a halogen atom, a substituted or unsubstituted linear, branched or cyclic alkyl group, a substituted or unsubstituted aryl group, a substituted or unsubstituted heteroaryl group, or a substituted or unsubstituted linear, branched or cyclic alkenyl group, a hydroxyl group, an alkoxy group, an amino group, a cyano group, a carbonyl group, a carboxyl group or an ester group; provided that two $R^{11}$s bonded to two adjacent carbon atoms on the benzene ring in the formula (7) may be bonded together to form a condensed ring with the benzene ring, and two adjacent $R^{12}$ and $R^{14}$ on the alkenyl group in the formula (8) may be bonded together to form a ring, and $R^{13}$ and $R^{14}$ bonded to the same carbon atom on the alkenyl group in the formula (8) may be bonded together to form a ring; b is an integer of 1 to 5; and Z represents a halogen atom, a methanesulfonate group or a trifluoromethanesulfonate group.

* * * * *